US006695829B2

(12) United States Patent
Hellstrom et al.

(10) Patent No.: US 6,695,829 B2
(45) Date of Patent: Feb. 24, 2004

(54) CONTAINER CLOSURE SYSTEM

(75) Inventors: Steven P. Hellstrom, Roselle, IL (US); Peter J. Karas, Libertyville, IL (US); John C. Tanner, II, Lake Bluff, IL (US)

(73) Assignee: Abbott Laboratories, Abbott Park, IL (US)

( * ) Notice: Subject to any disclaimer, the term of this patent is extended or adjusted under 35 U.S.C. 154(b) by 332 days.

(21) Appl. No.: 09/735,158

(22) Filed: Dec. 12, 2000

(65) Prior Publication Data

US 2001/0000347 A1 Apr. 19, 2001

Related U.S. Application Data

(62) Division of application No. 08/636,105, filed on Apr. 22, 1996, now abandoned.

(51) Int. Cl.$^7$ .......................... A61B 19/00; A61M 5/32; B65D 25/08; B65D 39/08; B65D 75/00

(52) U.S. Cl. ....................... 604/415; 604/403; 604/411; 604/414; 604/905; 206/222; 206/828; 215/356; 215/DIG. 3

(58) Field of Search ................................ 604/403, 411, 604/414–415, 249, 905, 239, 82, 83, 86–89, 90–92, 93.01; 215/355, 50, 53, 247, 249, 294, 299, 300, 370, 316, 321, DIG. 3, 250–251, 356; 220/377, 80; 206/215, 219, 229, 222, DIG. 8, 828; 141/326, 329, 27, 319, 383, 301, 310, 312

(56) References Cited

U.S. PATENT DOCUMENTS

| | | | |
|---|---|---|---|
| 2,342,215 | A | 2/1944 | Perelson |
| 2,388,634 | A | 11/1945 | Woody |
| 2,524,365 | A | 10/1950 | Smith |
| 2,608,972 | A | 9/1952 | Chrigstrom |

(List continued on next page.)

FOREIGN PATENT DOCUMENTS

| | | | |
|---|---|---|---|
| DE | 3152033 A1 | | 7/1983 |
| DE | 85 32 615.1 | | 2/1986 |
| EP | 0 311 787 | | 4/1987 |
| EP | 0 458 543 A1 | | 11/1991 |
| EP | 0 587 347 A1 | | 3/1994 |
| EP | 0 765 652 A1 | | 9/1995 |
| GB | 2 235 135 A | | 2/1991 |
| WO | WO 8404673 | * | 12/1984 |
| WO | WO 88/01881 | | 3/1988 |
| WO | WO 92/11056 | | 7/1992 |
| WO | WO 94/03373 | | 2/1994 |
| WO | WO 95/01197 | | 1/1995 |
| WO | WO 95/14176 | | 5/1995 |
| WO | WO 95/31242 | | 11/1995 |
| WO | WO 95/33505 | | 12/1995 |
| WO | WO 95/35125 | | 12/1995 |
| WO | WO 96/13301 | | 5/1996 |
| WO | WO 97/00702 | | 1/1997 |
| WO | WO 97/10156 | | 3/1997 |

*Primary Examiner*—Patricia Bianco
(74) *Attorney, Agent, or Firm*—Beth A. Vrioni

(57) ABSTRACT

A container closure system for delivering a fluid. The system includes a stopper constructed to seal fluidly a container. A closure member is mounted on an upper surface of the stopper. The closure member includes a base having an upper surface and a lower surface. The closure member further includes an outer wall and an inner wall extending from the upper surface of the base with the inner wall spaced from the outer wall. The base defines therethrough a needle access port between the inner and outer walls. The inner wall defines a chamber therein. The base further defines therethrough an aperture adjacent the chamber defined by the inner wall. A piercing member is movably disposed within the chamber defined by the inner wall. The piercing member has a first end portion and a second end portion, the first end portion being positioned proximally to the stopper. A piercing tip is mounted on the first end portion and is constructed to pierce the stopper. The second end portion of the piercing member is configured to engage a luer inserted into the chamber defined by the inner wall. A channel is defined through the piercing member.

11 Claims, 6 Drawing Sheets

U.S. PATENT DOCUMENTS

| | | | | | |
|---|---|---|---|---|---|
| 2,659,370 | A | | 11/1953 | Smith | |
| 2,667,986 | A | | 2/1954 | Perelson | |
| 3,336,924 | A | | 8/1967 | Sarnoff et al. | |
| 3,610,297 | A | | 10/1971 | Reef et al. | |
| 3,810,469 | A | | 5/1974 | Hurschman | |
| 3,826,260 | A | | 7/1974 | Killinger | |
| 3,872,992 | A | | 3/1975 | Larson | |
| 3,940,003 | A | | 2/1976 | Larson | |
| 3,977,555 | A | | 8/1976 | Larson | |
| 3,995,630 | A | | 12/1976 | van de Veerdonk | |
| 4,048,999 | A | | 9/1977 | Kobel | |
| 4,067,440 | A | | 1/1978 | Lataix | |
| 4,153,057 | A | | 5/1979 | Kobel | |
| 4,412,623 | A | | 11/1983 | Schmidt | |
| 4,493,348 | A | | 1/1985 | Lemmons | |
| 4,505,709 | A | | 3/1985 | Froning et al. | |
| 4,507,113 | A | | 3/1985 | Dunlap | |
| 4,564,054 | A | | 1/1986 | Gustavsson | |
| 4,576,211 | A | | 3/1986 | Valentini et al. | |
| 4,588,403 | A | | 5/1986 | Weiss et al. | |
| 4,619,651 | A | * | 10/1986 | Kopfer et al. | 604/415 |
| 4,624,393 | A | | 11/1986 | Lopez | |
| 4,662,878 | A | | 5/1987 | Lindmayer | |
| 4,673,404 | A | | 6/1987 | Gustavsson | |
| 4,675,020 | A | | 6/1987 | McPhee | |
| 4,927,423 | A | | 5/1990 | Malmborg | |
| 4,932,937 | A | | 6/1990 | Gustavsson et al. | |
| 4,982,740 | A | | 1/1991 | Broden | |
| 4,995,521 | A | * | 2/1991 | von Schuckmann | 215/249 |
| 5,024,256 | A | | 6/1991 | Vadher | |
| 5,035,689 | A | | 7/1991 | Schroeder | |
| 5,060,704 | A | | 10/1991 | Rohrbough | |
| 5,060,812 | A | | 10/1991 | Ogle, II | |
| 5,088,996 | A | | 2/1992 | Kopfer | |
| 5,092,840 | A | | 3/1992 | Healy | |
| 5,169,385 | A | | 12/1992 | Turnbull | |
| 5,215,538 | A | | 6/1993 | Larkin | |
| 5,232,029 | A | | 8/1993 | Knox et al. | |
| 5,275,299 | A | | 1/1994 | Konrad et al. | |
| 5,279,576 | A | | 1/1994 | Loo et al. | |
| 5,297,599 | A | | 3/1994 | Bucheli | |
| 5,342,319 | A | | 8/1994 | Watson et al. | |
| 5,358,501 | A | | 10/1994 | Meyer | |
| 5,360,413 | A | | 11/1994 | Leason et al. | |
| 5,364,386 | A | | 11/1994 | Fukuoka et al. | |
| 5,397,303 | A | | 3/1995 | Sancoff et al. | |
| 5,409,125 | A | | 4/1995 | Kimber et al. | |
| 5,411,499 | A | | 5/1995 | Dudar et al. | |
| 5,415,374 | A | | 5/1995 | Carroll et al. | |
| 5,421,814 | A | | 6/1995 | Geary | |
| 5,423,791 | A | | 6/1995 | Bartlett | |
| 5,425,465 | A | | 6/1995 | Healy | |
| 5,429,256 | A | * | 7/1995 | Kestenbaum | 215/247 |
| 5,433,703 | A | | 7/1995 | Utterberg et al. | |
| 5,437,648 | A | | 8/1995 | Graves et al. | |
| 5,441,487 | A | | 8/1995 | Vedder | |
| 5,454,409 | A | | 10/1995 | McAffer et al. | |
| 5,454,805 | A | | 10/1995 | Brony | |
| 5,466,219 | A | | 11/1995 | Lynn et al. | |
| 5,470,319 | A | | 11/1995 | Mayer | |
| 5,470,327 | A | | 11/1995 | Helgren et al. | |
| 5,474,541 | A | | 12/1995 | Ritsky et al. | |
| 5,474,544 | A | | 12/1995 | Lynn | |
| 5,487,737 | A | | 1/1996 | Meyer | |
| 5,501,676 | A | | 3/1996 | Niedospial et al. | |
| 5,514,116 | A | | 5/1996 | Vaillancourt et al. | |
| 5,514,117 | A | | 5/1996 | Lynn | |
| 5,520,642 | A | | 5/1996 | Bigagli et al. | |
| 5,520,665 | A | | 5/1996 | Fleetwood | |
| 5,520,666 | A | | 5/1996 | Choundhury et al. | |
| 5,573,520 | A | | 11/1996 | Schwartz et al. | |
| 5,573,525 | A | | 11/1996 | Watson et al. | |
| 5,573,526 | A | | 11/1996 | Hess | |
| 5,616,129 | A | | 4/1997 | Mayer | |
| 5,616,130 | A | | 4/1997 | Mayer | |
| 5,620,434 | A | | 4/1997 | Brony | |
| 6,499,617 | B1 | * | 12/2002 | Niedospial et al. | 215/320 |
| 6,513,650 | B2 | * | 2/2003 | Mollstam et al. | 206/222 |

* cited by examiner

CONTAINER CLOSURE SYSTEM

This is a divisional of U.S. patent application Ser. No. 08/636,105, filed Apr. 22, 1996, now abandoned.

BACKGROUND OF THE INVENTION

The present invention is directed to a system for containing and delivering a fluid. More particularly, the present invention is directed to a closure system that permits the introduction and withdrawal of fluid from a container using an instrument having a blunt, luer-type connector.

Many pharmaceutical products are delivered to pharmacies in sealed containers such as vials, glass or plastic bottles, and flexible bags. Such containers can contain a powdered or lyophilized formulation of a pharmaceutical product that must be reconstituted prior to administration to a patient. In addition, such containers can contain a solution formulation of a pharmaceutical product that can be withdrawn from the container and administered directly to a patient, for example, by parenteral administration.

Most pharmaceutical vials are fluidly sealed by a pierceable stopper, thereby isolating the contents of the vial from the vial's external environment. In order to access the pharmaceutical product within the vial, it is necessary either to pierce the stopper or to remove the stopper from the vial. However, removal of the stopper results in exposure of the pharmaceutical product to the external environment of the vial, thereby compromising the sterility and/or stability of the pharmaceutical product within the vial. For this reason, it often is preferable to access the pharmaceutical product by piercing the stopper.

The piercing of vial stoppers typically has been achieved through the use of sharp, small-bored needles. Standard hypodermic needles are particularly useful for this purpose because they allow the pharmaceutical product to be aseptically withdrawn from the vial and parenterally administered directly to a patient using a single device, thereby minimizing the risk of contamination of the pharmaceutical product. However, hypodermic needles pose a risk of inadvertent needle sticks to medical professionals. Due to growing concerns regarding the possible transmission of HIV and other diseases through needle sticks, there has been a significant trend away from the use of hypodermic needles. In addition, in many cases it is necessary to clean the outer surface of the vial stopper prior to piercing in order to reduce the risk of infection to the patient. This requires the medical professional to perform two distinct steps in order to withdraw the pharmaceutical product from the vial.

Various systems have been developed in order to eliminate the use of hypodermic needles in reconstituting and/or withdrawing pharmaceutical products from vials. For example, U.S. Pat. No. 5,171,214 discloses a system having a cannula surrounded by a protective skirt assembly, thereby reducing the possibility of an inadvertent needle stick. Other systems employ pre-slit stoppers that can be pierced using blunt cannulas, thereby obviating the need for a hypodermic needle. Still other systems, such as that disclosed in U.S. Pat. No. 2,342,215, permit blunt needle access to the contents of a vial through the use of a piercing member disposed within a stopper, the piercing member being activated through the application of an inwardly directed force using the blunt needle.

SUMMARY OF THE INVENTION

The system of the present invention provides a closure system for a container. The system includes a stopper having a lower surface configured to seal fluidly a container. A closure member is mounted on an upper surface of the stopper. The closure member includes a base, a lower surface of which is configured to engage the upper surface of the stopper. The closure member further includes an inner wall and an outer wall extending from an upper surface of the base, the inner wall being spaced from the outer wall. A needle access port is defined through the base of the closure member at a position between the inner and outer walls. In addition, an aperture is defined through the base at a position adjacent to a chamber defined by the inner wall. The system further includes a piercing member that is movably disposed within the chamber defined by the inner wall. The piercing member has a first end portion and a second end portion. A piercing tip is mounted on the first end portion, the piercing tip being configured to pierce the stopper. The second end portion is configured to engage a luer inserted into the chamber defined by the inner wall. A channel is defined through the piercing member such that fluid can be moved therethrough.

In an alternative embodiment of the present invention, the closure system includes a stopper having a lower surface configured to seal fluidly a container. A closure member is mounted on an upper surface of the stopper. The closure member includes a base, a lower surface of which is configured to engage the upper surface of the stopper. The closure member further includes a wall extending from an upper surface of the base. The wall defines a chamber therein. An aperture is defined through the base at a position adjacent to the chamber defined by the wall. The system also includes a piercing member movably disposed within the chamber defined by the wall. The piercing member has a first end portion and a second end portion. A piercing tip is mounted on the first end portion, the piercing tip being configured to pierce the stopper. The second end portion of the piercing member is configured to engage a luer inserted into the chamber defined by the wall. A channel is defined through the piercing member such that fluid can be moved therethrough. The system further includes a sealing member fluidly sealing the chamber defined by the wall.

BRIEF DESCRIPTION OF THE DRAWING

For a more complete understanding of the present invention, reference may be had to the following Detailed Description read in connection with the accompanying drawings in which.

DETAILED DESCRIPTION

Figure 1:
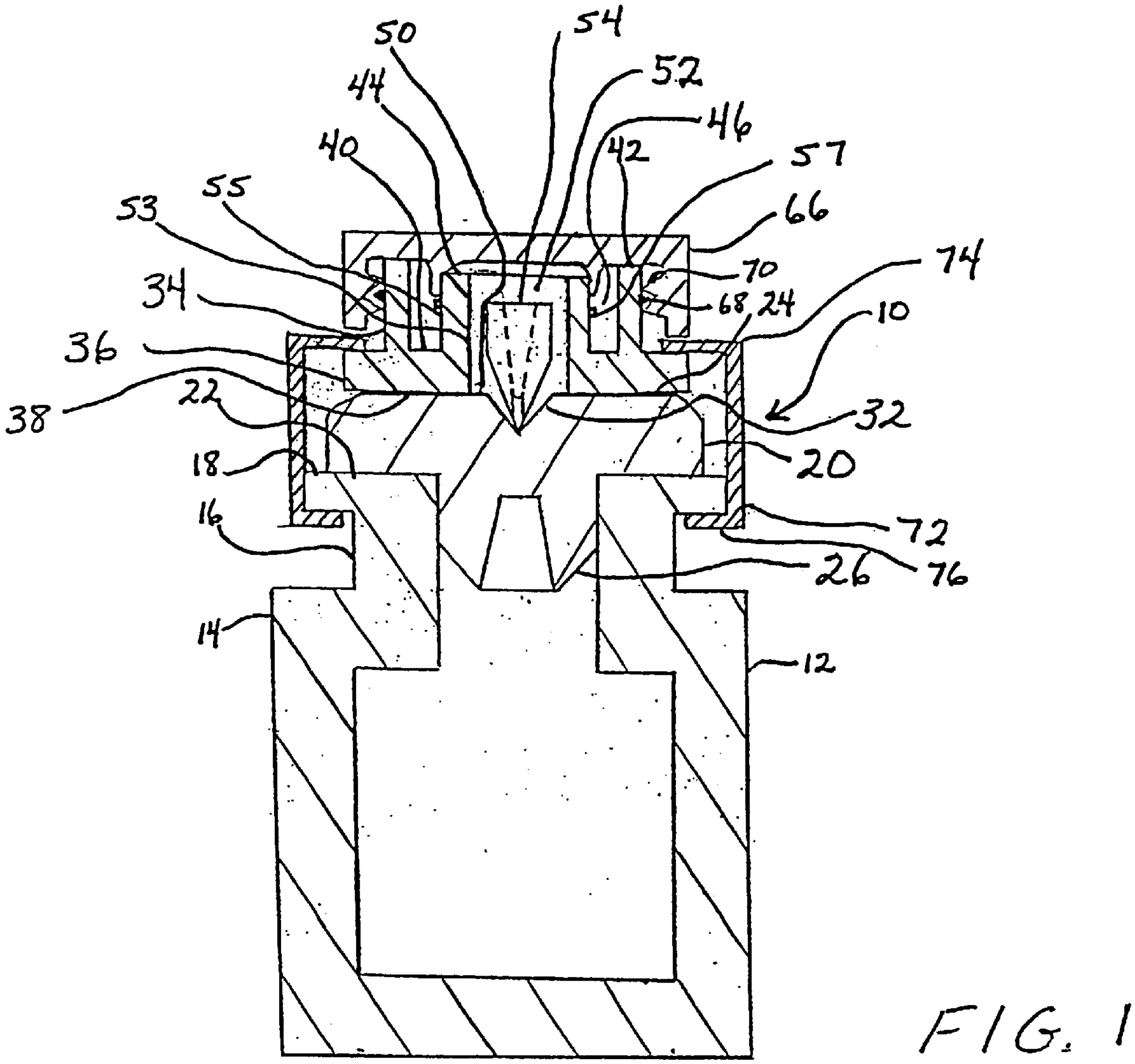
FIG. 1 is a cross-sectional view of a first embodiment of a container closure system constructed in accordance with the present invention.

A container closure system constructed in accordance with the present invention is generally indicated at 10 of FIG. 1. System 10 is configured to seal fluidly container 12. As depicted in the attached figures, container 12 can be a pharmaceutical vial of known construction. However, it will be appreciated that system 10 can be adapted to seal a wide variety of containers. The depiction herein of a pharmaceutical vial is not intended to be limiting, but instead represents one useful application of the system of the present invention. Container 12 also can be a plastic or glass bottle or a flexible bag of known construction. For the purposes of this disclosure, all references to container 12 include vials, bottles, and flexible containers.

As depicted in FIG. 1, container 12 is a vial and includes an upper end portion 14 having a neck portion 16 and an upper surface 18. Container 12 can be constructed of a variety of known materials using manufacturing techniques that form no part of the instant invention.

System 10 includes stopper 20 having lower surface 22 and upper surface 24. Lower surface 22 is configured to seal fluidly container 12. It will be appreciated that the configuration of stopper 20 will vary depending upon the nature and configuration of the container which it seals. For example, stopper 20 can be a pierceable membrane or plug configured to seal fluidly a port formed through a bottle, a flexible bag, or a vial. In addition, stopper 20 can be a pierceable membrane covering apertures and needle access ports constructed in accordance with the present invention, as discussed in detail herein.

In the embodiment of the present invention depicted in FIG. 1, lower surface 22 is configured to engage upper surface 18 of container 12 where container 12 is a vial. In addition, stopper 20 includes plug portion 26 extending from lower surface 22. As depicted in FIG. 1, plug portion 26 can be an annular wall. Plug portion 26 preferably has an outside dimension that is equal to or greater than an inner dimension of container 12, thereby providing a fluid-tight seal between plug portion 26 and container 12. Stopper 20 can be constructed of a variety of materials, provided that the material used is pierceable, as discussed in detail herein, and provided the material is capable of sealing fluidly container 12. For example, stopper 20 can be constructed of an elastomeric material having a capacity to provide a fluid-tight seal for container 12. Although lower surface 22 of stopper 20, as depicted in FIG. 1, includes plug portion 26, it will be appreciated that various configurations of stopper 20 can be used in connection with the system of the present invention without departing from the intended spirit and scope of the invention as set forth in the appended claims. For example, lower surface 22 of stopper 20 can be substantially planar.

Stopper 20 also can be in the form of a film seal which fluidly seals container 12. For example, elastomeric and metallic seals of known construction can be used to provide the requisite fluid-tight seal. In those embodiments of the present invention in which stopper 20 is a film seal, stopper 20 is preferably sealed against upper surface 18 of container 12 using known sealing methods, e.g., adhesives, thereby facilitating the sealing process. In some cases it may be preferable that stopper 20 is peelable from upper surface 18 of container 12. Further, in those embodiments of the present invention in which stopper 22 is configured to seal fluidly apertures and needle access ports formed through a container closure member constructed in accordance with the present invention, stopper 22 is preferably sealed to the closure member about the peripheries of each of the apertures and needle access ports. Various other modifications to the configuration of stopper 20 will be apparent to one of ordinary skill in the art.

In the embodiment of the present invention depicted in FIG. 1, the thickness of stopper 20 is reduced by indentation 32 formed in upper surface 24 of stopper 20. The utility of indentation 32 will be discussed in detail herein. It will be appreciated that a reduction in the thickness of stopper 20 also can be achieved by the formation of an indentation on lower surface 22, or by indentations on both lower surface 22 and upper surface 24.

System 10 of the present invention further includes closure member 34 mounted on stopper 20. Closure member 34 and stopper 20 can be integrally formed, attached to one another, for example, by way of adhesive or by way of a mechanical attachment such as a threaded attachment, or formed from separate, unbonded members without departing from the intended spirit and scope of the invention claimed herein. In the embodiment of the present invention depicted in FIG. 1, closure member 34 includes base 36 having lower surface 38 and upper surface 40. Lower surface 38 is configured to contact upper surface 24 of stopper 20. Closure member 34 can be constructed of a variety of known materials, including flexible plastics, rigid plastics, and metals.

In the first embodiment of the present invention depicted in FIG. 1, outer wall 42 and inner wall 44 extend from upper surface 40 of base 36. Outer wall 42 is spaced from inner wall 44 such that walls 42, 44 define a space 46 therebetween. In the embodiment of the present invention depicted in FIG. 1, walls 42, 44, and space 46 are annular in cross-section. However, it will be appreciated that walls 42, 44 can have a variety of shapes without departing from the intended spirit and scope of the present invention as claimed herein. In the depicted embodiment, space 46 is annular. The heights of walls 42 and 44 can be either the same or different. In the embodiment depicted in FIG. 1, the height of outer wall 42 is greater than the height of inner wall 44.

Figure 2:
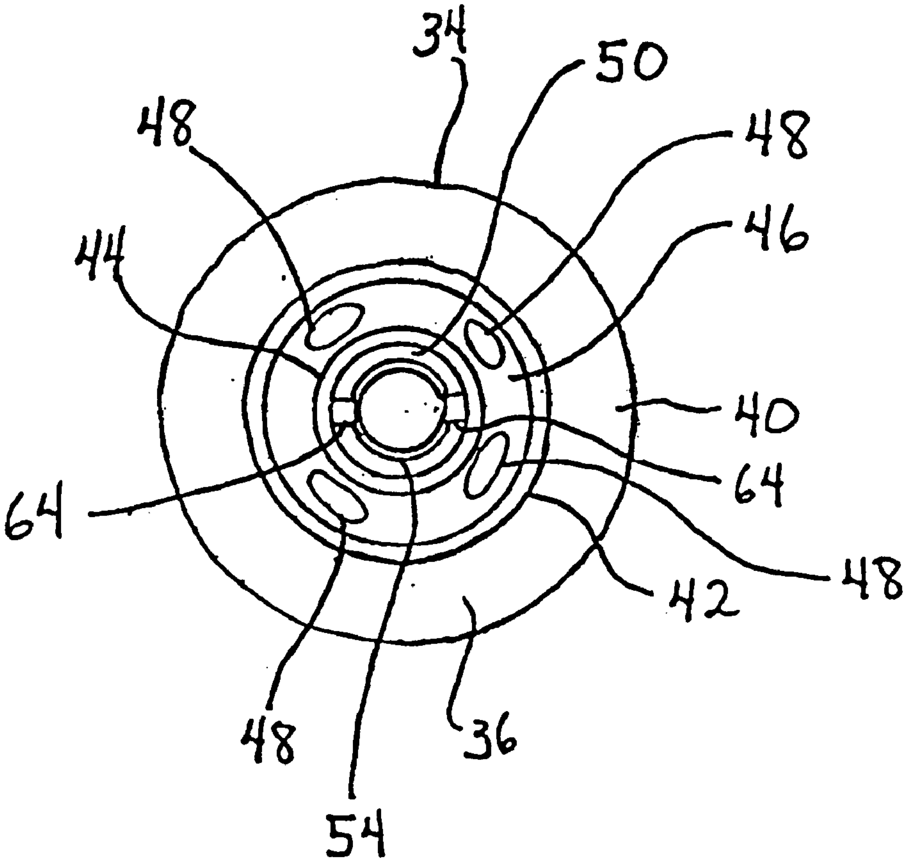
FIG. 2 is a top view of the first embodiment of a container closure system constructed in accordance with the present invention.

As depicted in FIG. 2, base 36 of closure member 34 defines therethrough one or more needle access ports 48 between walls 42, 44. It will be appreciated that the upper surface of stopper 20 is exposed to space 46 through needle access port 48, thereby enabling the withdrawal of fluid from container 12 using a hypodermic needle by inserting the needle through needle access port 48 and through stopper 20.

Inner wall 44 defines therein chamber 52. In the embodiment of the present invention depicted in the accompanying figures, chamber 52 is circular in cross-section. Base 36 defines therethrough aperture 50 at the base of chamber 52 defined by inner wall 44, thereby providing direct access from chamber 52 to stopper 20 through aperture 50. In the embodiment of the present invention depicted in FIG. 1, aperture 50 is adjacent to indentation 32 formed in upper surface 24 of stopper 20.

Inner wall 44 has an inner surface 53 and an outer surface 55. Inner wall 44 of the preferred embodiment of the present invention can have a variety of configurations, including cylindrical, conical, and combinations of cylindrical and conical configurations. In the preferred embodiment of the present invention, inner surface 53 of inner wall 44 also can be cylindrical, conical, or a combination of cylindrical and conical. However, it will be appreciated that inner wall 44 and inner surface 53 thereof can have a variety of configurations without departing from the scope of the present invention.

In the preferred embodiment of the present invention, inner surface 53 is dimensioned and configured to provide a frictional, substantially fluid-tight seal with an outer surface of luer 63 when luer 63 is inserted into chamber 52. Luers 63 currently used in the medical field typically conform to national and international standards and are configured either for slip or locking engagement. Male and female luers are tapered in order to provide a frictional fit therebetween. Thus, in the preferred embodiment of the present invention, at least a portion of inner surface 53 of inner wall 44 is conically shaped and is tapered in the direction of aperture 50 to provide a frictional, preferably fluid-tight fit with an outer surface of luer 63. In the preferred embodiment, the degree of taper of inner surface 53 of inner wall 44 is selected to match the taper of the male luer connector, thereby providing the desired sealing fit with the outer surface of luer 63 when luer 63 is inserted into chamber 52.

In an alternative embodiment of the present invention, outer surface 55 of inner wall 44 is configured to be releasably lockable to luer 63, thereby preventing luer 63 from being forced outwardly relative to chamber 52 when air is injected into container 12 or when container 12 is pre-pressurized. Locking engagement between luer 63 and outer surface 53 can be provided using a variety of known techniques, including threads and collars. In the embodiment of the present invention depicted in FIG. 1, outer surface 55 includes threadable member 57 which permits a threaded luer 63 to be threadably secured thereto. In one embodiment of the present invention, a single thread is provided on outer surface 55. In alternative embodiments of the present invention, threads can be provided at any position along outer surface 55, or along the entirety of outer surface 55, in order to provide the capacity to threadably secure luer 63 thereto. It will be appreciated that luer 63 can be selectively, threadingly released from outer surface 55 in these embodiments of the present invention when luer 63 is to be withdrawn from inner wall 44. Outer surface 55 alternatively can be configured to provide a snap fit with luer 63 such that luer 63 is releasably retained on outer surface 55. Such a snap fit can be provided by forming a collar on outer surface 53 of inner wall 44. It will be appreciated by one of ordinary skill in the art that various other mechanisms for maintaining the position of luer 63 with respect to inner wall 44 are possible.

Figure 3:
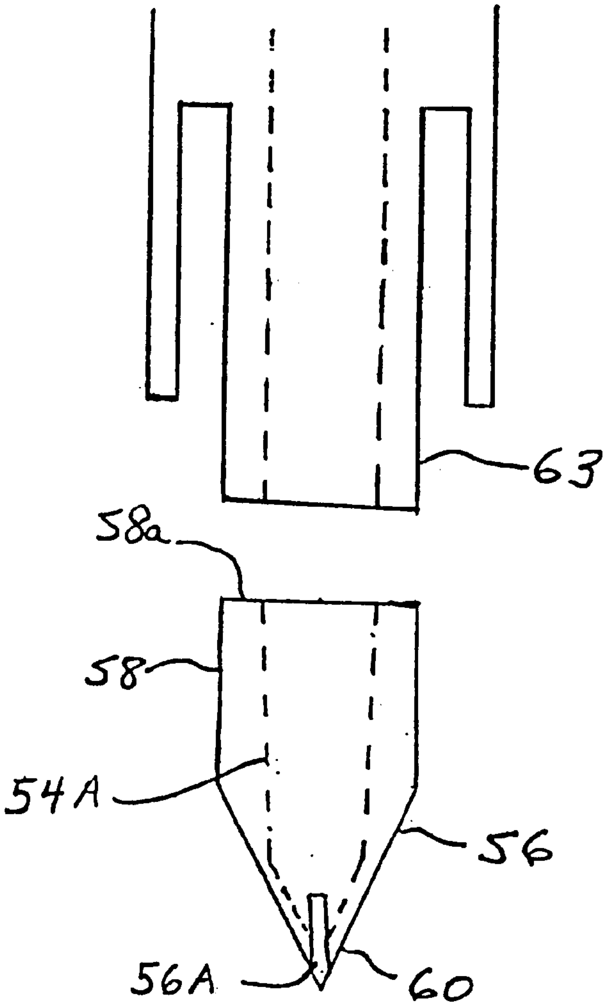
FIG. 3 is an elevational view of a piercing member and a luer connector constructed in accordance with the present invention.

Piercing member 54 is movably disposed within chamber 52 defined by inner wall 44. As depicted in FIG. 3, piercing member 54 includes first end portion 56 positioned proximally to stopper 20 and second end portion 58 positioned distally to stopper 20. Piercing tip 60 is mounted on first end portion 56 of piercing member 54. Piercing tip 60 can be integrally formed on piercing member 54, or piercing tip 60 can be attached to first end portion 56 of piercing member 54 through the use of known methods of adhesive or mechanical attachment. Second end portion 58 of piercing member 54 is configured to engage luer 63. In the preferred embodiment of the present invention depicted in the accompanying figures, second end portion 58 includes end surface 58a which is adapted to engage a terminal end of luer 63 in end-to-end abutment when luer 63 is inserted into chamber 52. A male-female connection between piercing member 54 and luer 63 is not necessary in the preferred embodiment of the present invention due to the fact that there is a frictional, substantially fluid-tight connection between luer 63 and inner wall 44. By eliminating the male-female luer connection between luer 63 and piercing member 54, the preferred embodiment reduces the possibility that piercing member 54 will be rotated by rotation of luer 63, thereby reducing the possibility that stopper 22 will be cored by rotation of piercing member 54.

Second end portion 58 of piercing member 54 can alternatively be configured to receive a male luer connector therein when luer 63 is a male luer connector. Second end portion 58 also can be configured to mate with a female luer connector when luer 63 is a female luer connector. In an alternative embodiment, second end portion 58 of piercing member 54 can be flared such that luer 63 can be placed either in end-to-end abutment therewith or in male-female engagement therewith. Second end portion 58 also can include a collar positioned about piercing member 54 where the collar is configured to provide either end-to-end abutment or male-female engagement with luer 63.

Piercing member 54 defines a channel 54A therethrough. Channel 54A enables fluid to be drawn through piercing member 54 from first end portion 56 to second end portion 58 for the removal of fluid from container 12 through luer 63. Channel 54A also enables fluid to be flowed through piercing member 54 from second end portion 58 to first end portion 56 for the introduction of fluid into container 12 from luer 63, e.g., during reconstitution of a lyophilized pharmaceutical product contained by container 12.

Figure 4:
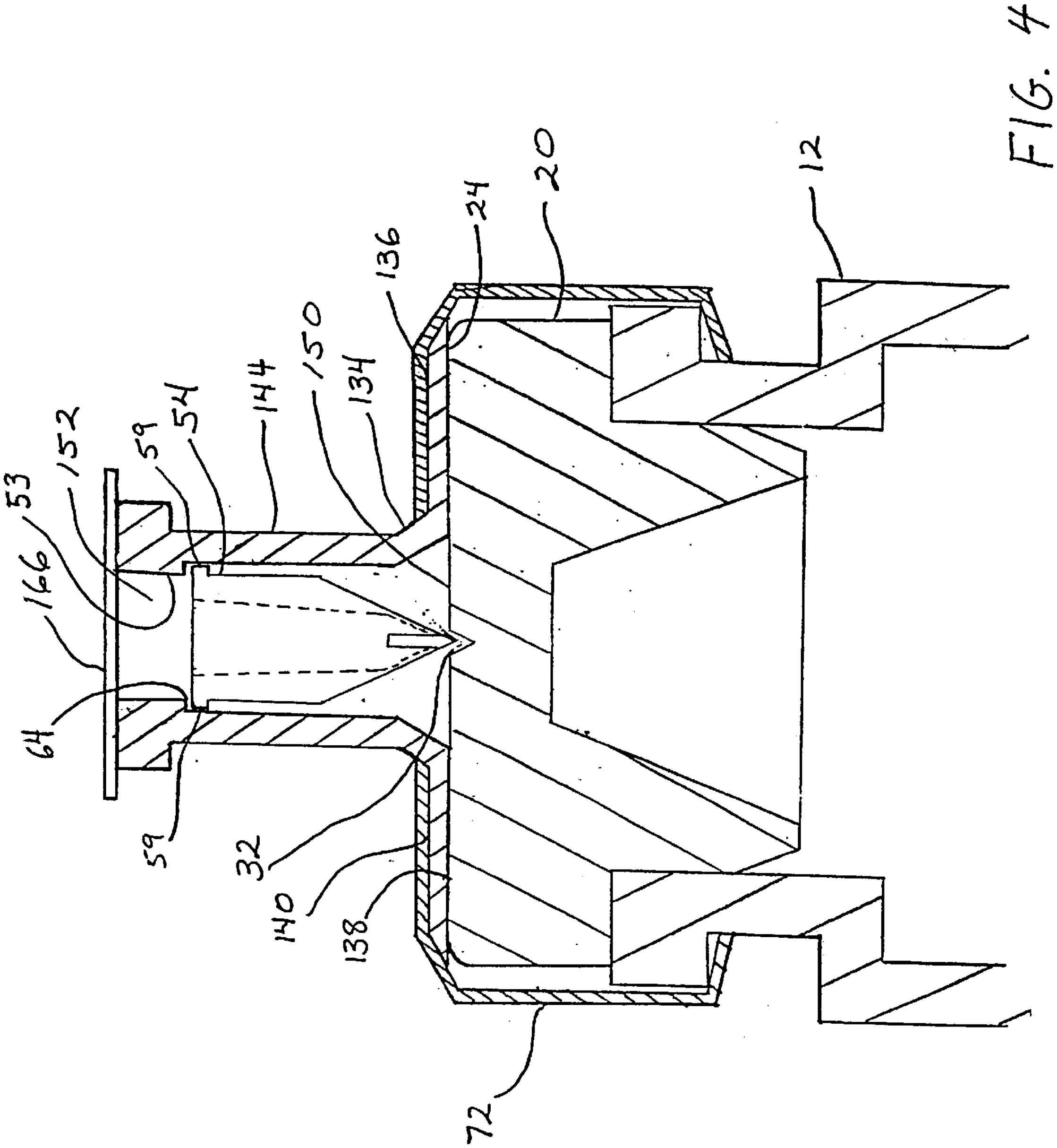
FIG. 4 is a cross-sectional view of a second embodiment of a container closure system constructed in accordance with the present invention.
Figure 5:
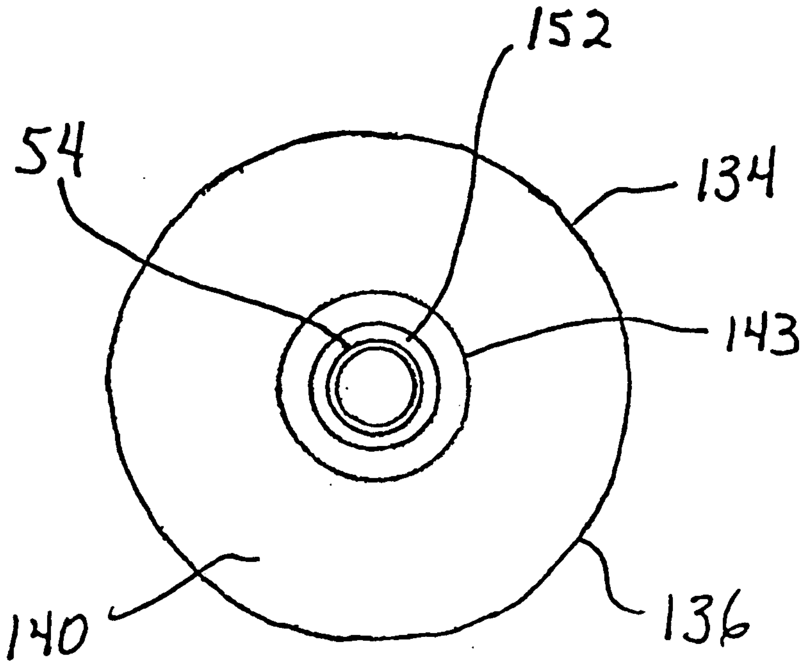
FIG. 5 is a top view of the second embodiment of a container closure system constructed in accordance with the present invention.
Figure 6:
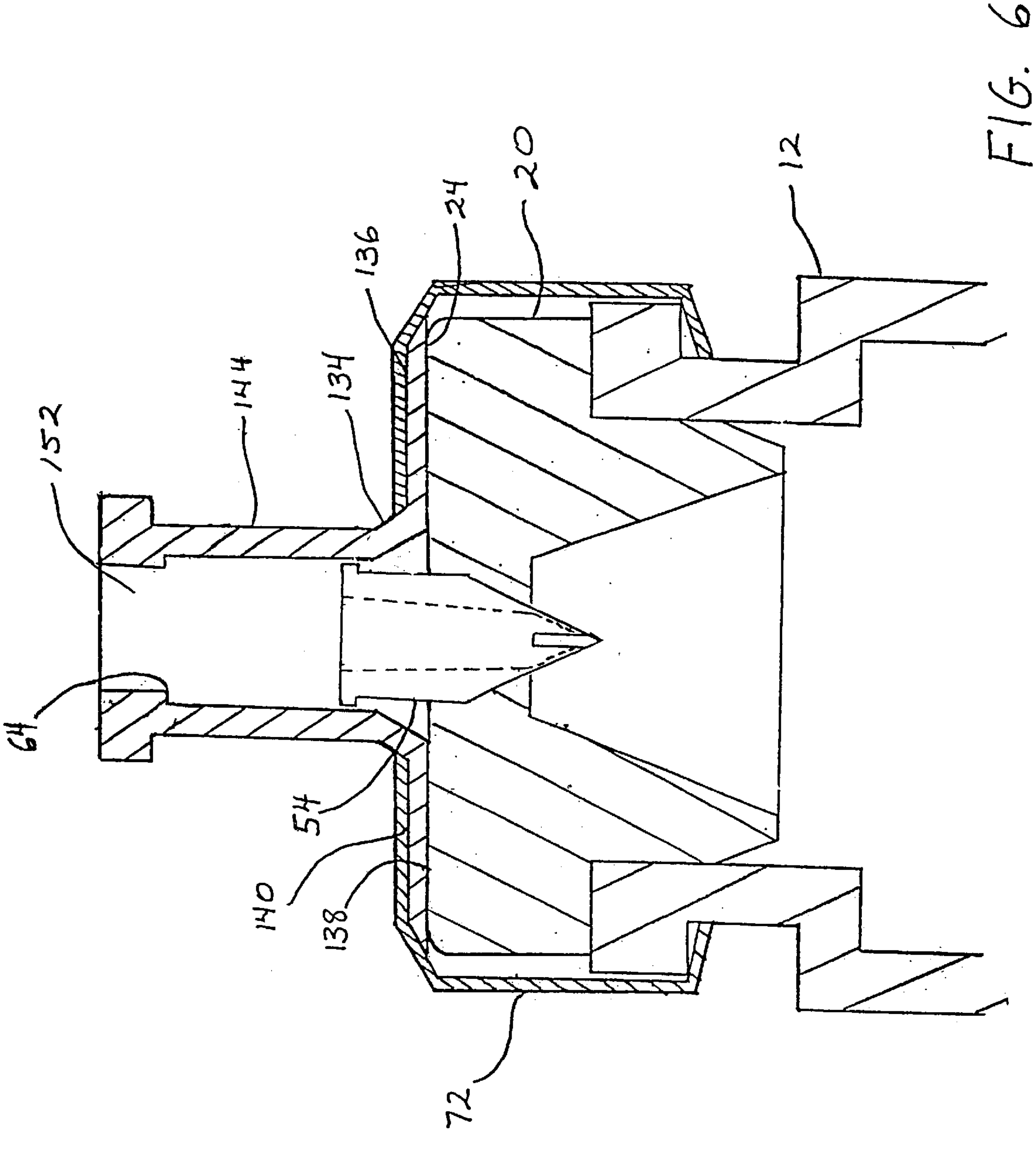
FIG. 6 is a cross-sectional view of the second embodiment of a container closure system constructed in accordance with the present invention in which the piercing member is in fluid contact with the interior of the container.

In the embodiment of the present invention depicted in FIG. 4, at least a portion of piercing member 54 frictionally engages inner surface 53 of inner wall 44. This frictional fit can be provided by constructing piercing member 54 such that its outer diameter is substantially equal to an inner diameter of inner wall 44, by positioning a collar having a diameter that is substantially equal to an inner diameter of inner wall 44 on piercing member 54, or by placing a plurality of frictional nibs 59 on piercing member 54 where the diameter of piercing member 54 plus frictional nibs 59 is substantially equal to an inner diameter of inner wall 44.

As above-indicated, the height of inner wall 44 can be substantially the same as or different than the height of outer wall 42. In one embodiment of the present invention, inner wall 44 and base 36 are configured such that either or both inner wall 44 and base 36 prevent luer 63 from forcing piercing member beyond a desired position relative to stopper 20 and container 12. In an alternative embodiment, a stop can be placed on exterior surface 55 of inner wall 44 in order to stop the forward motion of luer 63. In still another embodiment, piercing member 54 is configured such that it will not penetrate stopper 20 beyond a predetermined depth of penetration. For example, a collar can be provided on piercing member 54. It will be appreciated that the collar will riot pass readily through stopper 20 and thereby will impede forward motion of luer 63 and piercing member 54 relative to stopper 20 beyond a predetermined position. One of ordinary skill in the art will appreciate that other types of stops can be placed on piercing member 54 in order to impede the forward motion of luer 63 and piercing member 54 relative to stopper 20.

In an alternative embodiment of the present invention not depicted in the accompanying figures, stopper 20 is prepierced in order to facilitate movement therethrough of piercing member 54. In a second alternative embodiment of the present invention not depicted in the accompanying figures, piercing member 54 is mounted through stopper 20 such that first end portion 56 of piercing member 54 is in fluid contact with the contents of container 12. It will be appreciated that piercing tip 60 can be omitted in this second alternative embodiment of the present invention due to the fact that piercing member 54 is mounted through stopper 20. In this second alternative embodiment, piercing member 54 can include a luer accessible valve of known construction.

Port 56A is defined through first end portion 56 of piercing member 54 and is in fluid communication with channel 54A defined through piercing member 54. In the embodiment depicted in FIG. 3, port 56A extends a predetermined distance along first end portion 56 from piercing tip 60. When piercing member 54 is forced through stopper 20, port 56A is in fluid communication with fluid within container 12. In a preferred embodiment of the present invention, piercing member 54 and port 56A are configured such that port 56A extends at least from piercing tip 60 to a position substantially coincident with lower surface 22 of stopper 20 after piercing member 54 has been forced through stopper 20. In this way, substantially all fluid contained by container 12 can be withdrawn therefrom through piercing member 54, thereby reducing or eliminating waste. It will be appreciated that port 56A can have a variety of configurations without departing from the intended scope of the present invention.

Piercing member 54 preferably is configured such that it is retained by stopper 20 after piercing member 54 has been forced therethrough, thereby preventing piercing member 54 from being removed from closure member 34 when the luer 63 is removed from luer connection 62. In one embodiment of the present invention, piercing member retainer 64 in the form of a collar on inner wall 44 is provided in order to ensure that piercing member 54 is not inadvertently withdrawn from chamber 52. However, it will be appreciated that piercing member retainer 64 can have a variety of configurations. For example, piercing member retainer 64 can be disposed on first end portion 56 of piercing member 54. In this embodiment, piercing member retainer 64 is constructed such that it is able to pass through stopper 20 and into container 12 but thereafter cannot be withdrawn from stopper 20, thereby securing piercing member 54 to stopper 20.

As depicted in FIG. 1, indentation 32 defined by stopper 20 receives first end portion 56 of piercing member 54. Indentation 32 serves to orient and guide piercing member 54 with respect to stopper 20. In addition, indentation 32 reduces the thickness of stopper 20 that must be pierced by piercing member 54, thereby reducing the force required to pierce stopper 20.

Sealing member 66 is configured for removable attachment to closure member 34. Sealing member 66 can have a variety of configurations. In one embodiment, mating threads 68, 70 are formed on closure member 34 and sealing member 66, respectively, whereby sealing member 66 can be threadably secured to and removed from closure member 34. It will be appreciated that threads 68 can be formed on container 12 whereby sealing member 66 can be threadably secured to and removed from container 12. In a second embodiment, sealing member 66 is configured to provide a frictional or snap fit with closure member 34. In a third embodiment of the present invention depicted in FIG. 4, sealing member 66 is a peelable, preferably fluid-impervious membrane removably attached to closure member 34. Sealing member 66 may also include a tamper band.

In the embodiment of the present invention depicted in FIG. 1, sealing member 66 fluidly seals both outer wall 42 and inner wall 44 of closure member 34. In this way, chamber 52 defined by inner wall 44 remains fluidly isolated from space 46 when sealing member 66 is attached to closure member 34. However, in some cases it may not be necessary to isolate fluidly chamber 52 from space 46. Thus, sealing member 66 may also be constructed to seal fluidly only outer wall 42, thereby fluidly isolating the contents of container 12 from the external environment but not fluidly isolating chamber 52 from space 46. Sealing member 66 can be connected to closure member 34 to provide a flip-top seal, or sealing member 66 can be separate from closure member 34. Sealing member 66 preferably provides a sterile seal of closure member 34. The need to aseptically clean upper surface 24 of stopper 20 prior to use is obviated by maintaining the sterility of upper surface 24 of stopper 20 and piercing member 54 during storage, thereby reducing the labor associated with use of the system of the present invention.

As above-discussed, closure member 34 and stopper 20 can be integrally formed, attached to one another, for example, by way of adhesive, or formed from separate, unbonded members without departing from the intended scope of the invention claimed herein. In the embodiment of the present invention depicted in FIG. 1, closure member 34 and stopper 20 are separate, unbonded elements. In this embodiment, ferrule 72 is provided to secure closure member 34 and stopper 20 to container 12. Ferrule 72 includes first leg 74 and second leg 76 configured to grasp upper surface 40 and neck 16, respectively. Ferrule 72 thus retains container closure 34 and stopper 20 against upper surface 18 of container 12. In the event that stopper 20 is constructed of an elastomeric material, ferrule 72 can be configured to urge closure member 34 toward container 12, thereby compressing stopper 20 between closure member 34 and container 12, and thereby facilitating a fluid-tight seal between stopper 20 and container 12. Ferrule 72 can be constructed of a variety of known materials, including soft metals, such as aluminum, and plastics.

In the embodiment of the present invention depicted in FIG. 4, container 12 and stopper 20 are constructed as above-discussed with respect to the first embodiment of the present invention depicted in FIG. 1. This embodiment further includes closure member 134 having base 136. Base 136 has lower surface 138 configured to contact upper surface 24 of stopper 20. Base 136 further includes upper surface 140. Wall 144 extends upwardly from upper surface 140 and defines a chamber 152 therein. The configuration of wall 144 and its cooperation with a luer are the same as above-discussed in detail with respect to luer 63 and wall 44 of the embodiment of the present invention depicted in FIG. 1. Base 136 defines therethrough an aperture 150 at a position adjacent to chamber 152. Aperture 150 provides direct access to stopper 20 from chamber 152. As depicted in FIG. 4, stopper 20 includes indentation 32 defined by upper surface 24 of stopper 20.

Piercing member 54, constructed in accordance with the description of the embodiment of the present invention depicted in FIG. 3, is movably disposed within chamber 152 of the embodiment of the present invention depicted in FIG. 4. Sealing member 166 fluidly seals chamber 152 from an external environment of system 10. Sealing member 166 can have any of the configurations above-discussed with respect to sealing member 66 depicted in FIG. 1. As depicted in FIG. 4, sealing member 166 can be a peelable membrane.

Ferrule 72, constructed in accordance with the description of the embodiment of the present invention depicted in FIG. 1, retains closure member 134 and stopper 20 on container 12 as above-discussed.

Use of system 10 of the present invention will now be described. For the purposes of this description, reference will be made to the embodiment of the present invention depicted in FIG. 1. However, it will be appreciated that the discussion set forth herein also applies to the embodiment depicted in FIG. 4.

Sealing member 66 is removed from closure member 34, thereby exposing the interior of closure member 34. A medical professional can then access the contents of container 12 in one of two ways. First, the medical professional can withdraw fluid from container 12 using a sharp catheter, e.g., a hypodermic needle, by inserting the needle through needle access port 48 and piercing stopper 20. After insertion of the needle into container 12, fluid is drawn into the needle and the needle is withdrawn from stopper 20 through needle access port 48. Subsequent withdrawals of fluid from container 12 can be made using a needle by following the same sequence of steps.

In a second application of the system of the present invention, a medical professional will use a device having luer 63 mounted thereon. Luer 63 is inserted into chamber 52. As above-discussed, inner wall 44 and wall 144 are preferably configured to provide a fluid-tight seal with the exterior surface of luer 63 when luer 63 is inserted therein. The medical professional then applies pressure to luer 63 such that it engages piercing member 54 and forces piercing member 54 toward container 12, thereby causing piercing tip 60 to penetrate stopper 20. Upon penetration of stopper 20 by piercing tip 60, the contents of container 12 are in fluid communication with piercing member 54 which in turn is in fluid communication with luer 63. If luer 63 and the exterior surfaces of inner wall 44/wall 144 are threaded, luer 63 can be threadably secured to inner wall 44/wall 144. The medical professional then can inject fluid into container 12 and/or withdraw fluid from container 12 through piercing member 54 by operation of luer 63 and a syringe attached thereto. When the injection into and/or withdrawal of fluid from container 12 has been completed, the luer 63 is withdrawn from inner wall 44, wall 144. As above-discussed, in the preferred embodiment of the present invention, stopper 20 and piercing member 54 preferably are constructed such that piercing member 54 is not withdrawn from stopper 20 when luer 63 is withdrawn from the inner wall 44/wall 144. In the event that piercing member 54 is withdrawn from stopper 20 during this procedure, piercing member retainer 64 will prevent piercing member 54 from being removed from chamber 52.

The embodiment of the system of the present invention depicted in FIG. 1 allows a medical professional to access the contents of container 12 using either a sharp cannula or a device having luer 63 mounted thereon. The embodiment of the system of the present invention depicted in FIG. 4 allows a medical professional to access the contents of container 12 using only a device having luer 63 mounted thereon. However, the embodiment of the system of the present invention depicted in FIG. 3 can be modified to include one or more needle access ports 48 defined by base 136 of closure member 134, thereby providing direct access to stopper 20.

Although the present invention has been disclosed herein with respect to certain preferred embodiments, it will be apparent to one of ordinary skill in the art that various modifications can be made to the system of the present invention. These modifications are intended to be within the scope of the present invention as claimed in the accompanying claims.

What is claimed is:

1. A container closure system comprising:

a closure member configured to be attached to a container, said closure member comprising a base having an upper surface and a lower surface, said closure member further comprising an outer wall and an inner wall spaced from said outer wall, said outer wall and said inner wall extending from said upper surface of said base, said base defining therethrough a needle access port intermediate said inner and outer walls, said inner defining a chamber therein, said base defining therethrough an aperture adjacent said chamber defined by said inner wall;

a stopper means for fluidly sealing said needle access port and said aperture defined by said base of said closure member; and a piercing member movably disposed within said chamber defined by said inner wall, said piercing having a first end portion and a second end portion, said first end portion of said piercing member positioned proximally to said stopper means, a piercing tip mounted on said first end portion, said piercing tip constructed to pierce said stopper means, said second end portion constructed to engage a luer inserted into said chamber defined by said inner wall, said piercing member further defining a channel therethrough, said channel defined by said piercing member constructed to permit fluid transfer through said piercing member;

a sealing member fluidly sealing said chamber defined by said inner wall from an external environment of said chamber, wherein said closure member and said sealing member have mating threads formed thereon whereby said sealing member can be threadably secured to said closure member.

2. A container closure system in accordance with claim 1, wherein said base of said closure member defines therethrough a plurality of needle access ports intermediate said inner and outer walls.

3. A container closure system in accordance with claim 1, wherein said inner wall has an inner surface configured to engage frictionally a luer inserted into said chamber defined by said inner wall.

4. A container closure system in accordance with claim 3, wherein said second end portion of said piercing member has a terminal end, and wherein said inner surface of said inner wall and said piercing member are configured such that said luer inserted into said chamber defined by said inner wall engages said terminal end of said piercing member in end-to-end abutment.

5. A container closure system in accordance with claim 1, wherein said system further comprises a ferrule having a first leg and a second leg, said first leg engaging said closure member and said second leg configured to engage a container.

6. A container closure system in accordance with claim 1, wherein said sealing member comprises a peelable membrane.

7. A container closure system comprising;

a stopper having an upper surface and a lower surface, said lower surface configured to seal fluidly an aperture of a container;

a closure member mounted on said upper surface of said stopper, said closure member comprising a base having an upper surface and a lower surface, said closure member further comprising an outer wall and an inner wall spaced from said outer wall, said outer wall and said inner wall extending from said upper surface of said base, said lower surface of said base constructed to engage said upper surface of said stopper, said base defining therethrough a needle access port intermediate said inner and outer walls, said inner wall defining a chamber therein, said base defining therethrough an aperture adjacent said chamber defined by said inner wall; and a piercing member movably disposed within said chamber defined by said inner wall, said piercing member having a first end portion and a second end portion, said first end portion of said piercing member positioned proximally to said stopper, a piercing tip mounted on said first end portion, said piercing tip constructed to pierce said stopper, said second end portion constructed to engage a luer inserted into said chamber defined by said inner wall, said piercing member further defining a channel therethrough, said channel defined by said piercing member constructed to permit fluid transfer through said piercing member;

and a sealing member fluidly sealing said chamber defined by said inner wall from an external environment of said chamber, wherein said closure member and said sealing member have mating threads formed thereon whereby said sealing member can be threadably secured to said closure member.

8. A container closure system in accordance with claim 7, wherein said inner wall has an inner surface configured to engage frictionally a luer inserted into said chamber defined by said inner wall.

9. A container closure system in accordance with claim 8, wherein said second end portion of said piercing member has a terminal end, and wherein said inner surface of said inner wall and said piercing member are configured such that a luer inserted into said chamber defined by said inner wall engages said terminal end of said piercing member in end-to-end abutment.

10. A container closure system comprising:

a closure member configured to be attached to a container, said closure member comprising a base having an upper surface and a lower surface, said closure member further comprising an outer wall and an inner wall spaced from said outer wall, said outer wall and said inner wall extending from said upper surface of said base, said base defining therethrough a needle access port intermediate said inner and outer walls, said inner wall defining a chamber therein, said base defining therethrough an aperture adjacent said chamber defined by said inner wall and a plurality of needle access ports intermediate said inner and outer walls;

a stopper means for fluidly sealing said needle access port and said aperture defined by said base of said closure member; and a piercing member movably disposed within said chamber defined by said inner wall, said piercing member having a first end portion and a second end portion, said first end portion of said piercing member positioned proximally to said stopper means, a piercing tip mounted on said first end portion, said piercing tip constructed to pierce said stopper means, said second end portion constructed to engage a luer inserted into said chamber defined by said inner wall, said piercing member further defining a channel therethrough, said channel defined by said piercing member constructed to permit fluid transfer through said piercing member.

11. A container closure system in accordance with claim 10, wherein said inner wall has an inner surface configured to engage frictionally a luer inserted into said chamber defined by said inner wall.

* * * * *